United States Patent [19]

Ohnishi

[11] Patent Number: 4,840,968
[45] Date of Patent: Jun. 20, 1989

[54] PREPARATION AND USES OF NEW PROSTAGLANDIN DERIVATIVES WHICH PROTECT CELL MEMBRANES AGAINST ISCHEMIC, PHYSICAL, CHEMICAL, AND BIOLOGICAL INJURIES

[76] Inventor: Tsuyoshi Ohnishi, 502 King of Prussia Rd., Radnor, Pa. 19087

[21] Appl. No.: 147,839

[22] Filed: Jan. 25, 1988

Related U.S. Application Data

[63] Continuation-in-part of Ser. No. 104,713, Oct. 2, 1987, abandoned.

[51] Int. Cl.$^4$ .................. C07C 177/00; A61K 31/557
[52] U.S. Cl. .................................. 514/530; 560/116; 560/121
[58] Field of Search ................. 514/530; 560/116, 121

[56] References Cited

U.S. PATENT DOCUMENTS

| | | | |
|---|---|---|---|
| 4,153,808 | 5/1979 | Polis | 562/503 |
| 4,245,111 | 1/1981 | Polis | 560/121 |
| 4,338,466 | 7/1982 | Nelson | 568/343 |
| 4,663,486 | 5/1987 | Nelson | 508/353 |
| 4,668,828 | 5/1987 | Nelson | 568/353 |

OTHER PUBLICATIONS

Von Euler, Prostaglandins, pp. 20, 21, (1967).

*Primary Examiner*—Robert Gerstl
*Attorney, Agent, or Firm*—Caesar, Rivise, Bernstein, Cohen & Pokotilow, Ltd.

[57] ABSTRACT

The invention provides novel compounds which can protect (i) organs, such as the brain, spinal cord, heart, lung, liver, kidney, stomach, duodenum and blood vessels, (ii) skin cells, and (iii) circulating cells such as red blood cells and white blood cells from ischemic, physical, chemical and biological injuries either by pre-administation or post-administration. The compounds can also protect red blood cells from malarial parasites. The compounds are synthesized from prostaglandin $A_1$ or $E_1$ first by alkaline treatment to form free-acid molecules, and then by converting them to hydrophobic ester-form compounds. Comparing with free-acid compounds, the ester-form compounds have the following advantageous features: (a) Unlike free-acids, they do not form insoluble micelles with calcium in the blood stream; (b) they are more soluble in lipids than free-acids, thus they are more easily incorporated into cells; (c) they are more stable than free-acids; (d) they are hydrolyzed by endogeneous esterases upon entering the cells, thereby forming the free-acid molecules within the cells. This causes continuous accumulation within the cells. This causes continuous accumulation of free-acid molecules within the cells, and makes their concentration higher than the external concentration of original ester-form compounds. Thus, they can manifest high efficacy; (e) the free-acid molecules thus accumulated within the cells protect the cell membranes by chelating calcium ions, by inhibiting membrane-degradating enzymes and by inhibiting undesirable enzymic reactions within the cell. These compounds can be administered orally, subcutaneously, intramuscularly, intravenously or topically. These compounds can also be used to protect organs during transplant surgery by administering to the donor before removal of the organ and by administering to the receipient after transplantation.

6 Claims, 10 Drawing Sheets

Fig. 1

PERFUSED RAT HEART MODEL

PREPARATION AND USES OF NEW PROSTAGLANDIN DERIVATIVES WHICH PROTECT CELL MEMBRANES AGAINST ISCHEMIC, PHYSICAL, CHEMICAL, AND BIOLOGICAL INJURIES

BACKGROUND OF THE INVENTION

This application is a continuation-in-part application based on prior filed U.S. application Ser. No. 104,713 filed Oct. 2, 1987,

FIELD OF THE INVENTION

The present invention relates to new compounds, which are synthesized from prostaglandin $A_1$ or prostaglandin $E_1$, as well as to methods of administering these compounds to protect organ cells, skin cells and circulating cells from various ischemic, physical, chemical and biological injuries.

BACKGROUND ART

It has been well documented that ischemic, physical, chemical and biological injuries cause an increase of intracellular calcium concentration in the cells, which in turn activates endogeneous phospholipases and proteases. These enzymes not only attack cell membranes causing injury, but also initiate a cascade of reactions whose metabolites could cause thrombosis, inflammation, allergy, ulcer and immune deficiency. The inventor synthesized new compounds from prostaglandin $A_1$ or prostaglandin $E_1$ which can protect cells by (a) chelating intracellular calcium ions, (b) inhibiting phospholipase and protease activities and (c) inhibiting various endogeneous enzymes which are involved in the cascade of reactions. The compounds were also found to protect organs of chronic alcoholic subjects.

SUMMARY OF THE INVENTION

Prostaglandin $A_1$ or prostaglandin $E_1$ monomers were polymerized with an alkaline treatment. The number of monomers contained in the oligomer was 3–7. These compounds are abbreviated as MR-256 (acid-form molecules). Acid-form molecules have some therapeutic efficacies to protect cells from ischemia, but they have several disadvantages: (a) When administered, they form insoluble calcium micelles in the blood stream, which lowers effective blood concentration; (b) They are easily bound by proteins and lipids in the serum, thus their effective blood concentration is lowered; (c) Being free-acid molecules, they are water soluble. Thus, it is difficult to attain high permeability to cross cell membranes; (d) Free-acids are unstable, and tend to lose activity during storage. The inventor solved these problems by converting these acid-form compounds into hydrophobic esters. The ester-form compounds are abbreviated as MR-356.

The ester-form compounds can be administered orally, subcutaneously, intramuscularly, intravenously or topically. The ester-form compounds thus administered enter cells through the membranes, because these compounds have high affinity to lipids. Then, the compounds are decomposed inside the cells by cellular enzymes to become acid-form molecules. Since the acid-form molelcules are less lipid soluble, they tend to stay inside the cells.

Compared to acid-form compounds, the ester-form compounds were found to have the following new properties which make these compounds very unique:

(a) Compounds are highly soluble to cell membranes and easily transported into cells, (b) When transported into cells, the ester-molecules are decomposed to acid-form molecules by endogeneous esterase enzymes, (c) Thus created acid-form molecules are less soluble to a lipid phase so that they will stay inside the cell, (d) Since the acid-form molecules keep accumulating within the cells, their intracellular concentration will become much higher than the extracellular concentration of ester-form molecules. This makes the administration of ester-form molecules much more efficacious than that of acid-form molecules.

(e) The staying acid-form molecules can chelate calcium, thus protect injured cells from calcium-toxicity.

(f) The staying acid form molelcules inhibit the endogeneous phospholipase $A_2$ activity, thereby inhibiting the formation of arachidonic acid. Since arachidonic acid is known to initiate a cascade of reactions producing prostaglandins, prostacyclines, leukotrienes and lypoxins, which are known to have high biological activities to cause pathologic conditions such as thrombosis, inflammation, allergy, ulcer and immune deficiency, the staying acid-form molecules can ameliorate these pathologic conditions.

(g) The staying acid-form molelcules can directly inhibit various endogeneous enzymes involved in these reactions, thus protecting the cells from injury and degradations.

The inventor tested efficacy of these new compounds in various animal experiments as well as in in vitro experiments, which include:

(i) protection of the brain from ischemic damages, (ii) protection of the perfused heart model from ischemic damage, (iii) protection of isolated heart cells from ischemic damage, (iv) protection of the kidney from damage caused by ischemia as well as by various chemicals including alcohol, (v) protection of the liver from ischemic damage, (vi) protection of the spinal cord from contusion injury, (vii) protection of sickle red blood cells from sickling-unsickling damage, (viii) protection of organs of chronic alcoholics, (ix) Protection of red blood cells from infection by malarial parasites, (x) protection of the skin from physical damage.

DETAILED DESCRIPTION OF THE INVENTION

Examples of this invention are set forth below. However, it is to be understood that these examples are given by way of illustration only and are not to be construed as limiting the invention either in spirit or in scope, as many modifications both in composition of reagents and methods could be possible to those skilled in the art.

DRUG PREPARATION METHOD (a) A compound (which is called in this application as MR-256 for identification purpose) was synthesized from prostaglandin $A_1$ or prostaglandin $E_1$ using a method similar to that developed by Polis and Polis, who prepared acid-form oligomers from prostaglandin B₁ (U.S. Pat. No. 4,153,808). In brief: 0.1 g of prostaglandin A$_1$ or prostaglandin E$_1$ was dissolved in 10 ml ehtanol and added to 1.2 g crushed solid KOH in a 50 ml flask. The mixture was rotated on a reflux apparatus at 70° C. for three hours. Ten ml of water was added to make the final base concentration 1 N KOH in 50% alcohol and the mixture was refluxed in an oil bath at 74° C. for an additional 6 hours. The reaction mixture was cooled to room temperature. 11 ml isobutanol was added and adjusted the pH 3 with addition of about 7.5 ml 2.3 N HClO$_4$. The precipitate that formed was allowed to settle, the supernatant decanted and the precipitate washed with H$_2$O and a small amount of alcohol until white. The precipitate was discarded and the colored supernatant and washing combined with an additional 20 ml H$_2$O, 10 ml of isobutanol and extracted at pH 3. The clear H$_2$O layer was discarded. The red isobutanol layer was washed twice with 10 ml of water and finally extracted with 25 ml of 0.1 M NaHCO$_3$ freshly prepared (ph 8.5). 10 ml of isobutanol was added to the separated NaHCO$_3$ solution which contains oligomers, and the pH adjusted to 3 with 2.7 ml of 1 N HCl. The active components were then all extracted into the isobutanol layer which was washed with H$_2$O, dried and flash evaporated to yield a compound which is defined as Mr-256. This compound is in an acid form. The molecular weight of this compound as determined by vapor pressure osmometry is about 2,200 suggesting that the major component of this compound may be hexamers, although trimer, tetramer, pentamer and heptamer are also contained. The yield was 70–80%.

(b) Preparation of hydrophobic ester-form of MR-256 was done as follows: 50 mg of MR-256 was mixed with 0.5 ml of ethyldiisopropylamine, 0.1 ml chloroform, and 2 ml of isobutanol. Then 0.2 ml of acetoxymethyl bromide or acetoxyethyl bromide was added and the mixture was stirred in a stoppered flask for 20h. The solution was evaporated in vacuo, the residue taken up in benzene, filtered to remove the unnecessary product, ethyldiisopropylammonium bromide, and reevaporated. The residue was extracted with diethyl ether several times. The extracts were combined, and evaporated in vacuo overnight. The yield from the free acid compound is 60–70%. This ester-form is denoted as MR-356 for an identification purpose. MR-356 is not water soluble, but soluble in ethanol.

(c) Thinlayer chromatography: Compounds MR-256 and MR-356 were developed on a silica gel thin layer plate using a mixture of benezene and methanol (ratio 2:1). MR-256 remained at the origin, whereas the Rf value for MR-356 was 0.69. This result confirms that the ester-form compound is much more hydrophobic than the original acid compounds.

(d) Toxicity: We injected (i.p.) a high dose of MR-256 or MR-356 (70 mg/kg body weight) to five mice each. No toxicity was observed; the animals behaved normally.

EXPERIMENTAL DESIGN AND RESULTS

EXAMPLE 1

Figure 1:
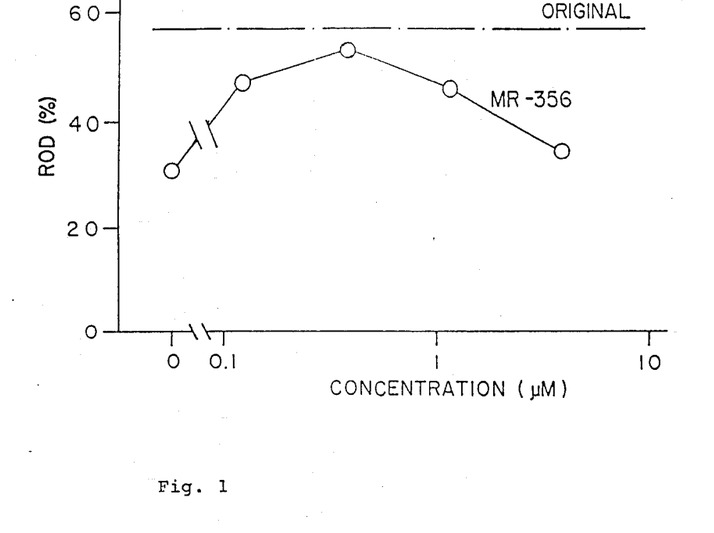
FIG. 1 Dose-response curve of the effect of MR-356 against damages of myocytes caused by 1 hour ischemia. The intactness of myocytes was assessed by the percentage of rod-shaped cells.

PROTECTIVE EFFECTS IN HEART ISCHEMIA (a) Protection of myocytes:

Myocytes (isolated cardiac cells) were prepared from the rat heart according to the method of Hohl, C., Alatschuld, R. A. and Brieley, G. P., (Arch. Biochem. Biophys. 221:197–205, 1983). About 60 to 70% of myocytes were in rod-shape form (a rod-shape indicates intactness of isolated cardiac cells). When these myocytes were kept under nitrogen for 1 hour, about half of the rod-shaped cells were irreversibly damaged and turned into round-shaped cells. If MR-356 was added to the suspension before the nitrogen exposure, formation of round-shaped cells was inhibited. At concentrations less than 1 uM, the drug protected myocytes from this ischemic damage as indicated by the preservation of rod-shaped cells in FIG. 1.

Figure 2:
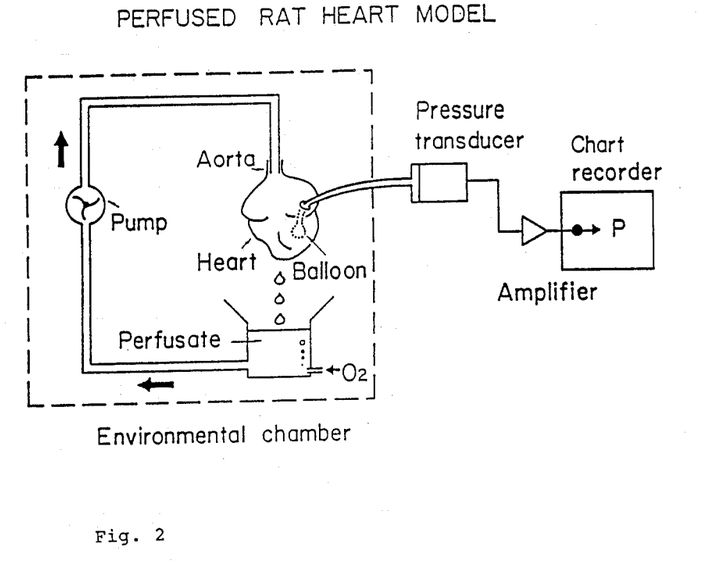
FIG. 2 Schematic illustration of perfused rat heart model.
Figure 3:
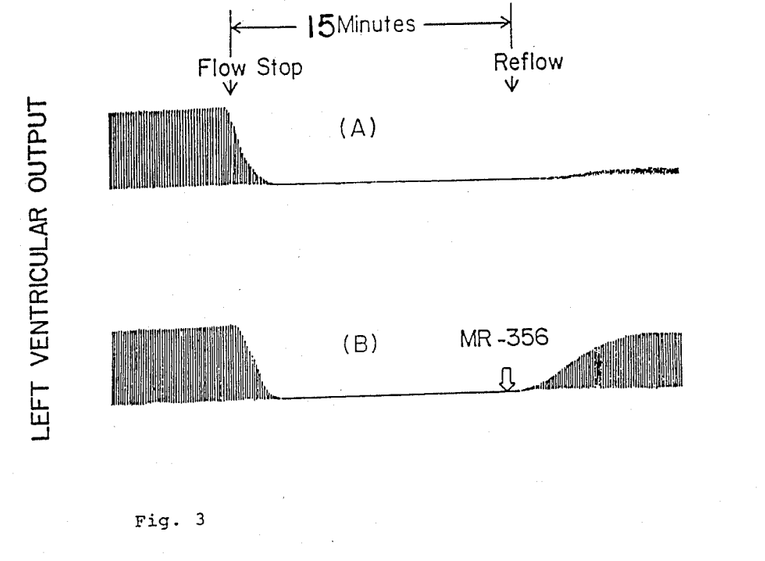
FIG. 3 Left ventricular output of beating hearts before and after 15 minutes ischemia. (A) without drug, (B) 3.8 uM MR-356 was added before reflow. Temperature 37° C.
Figure 4:
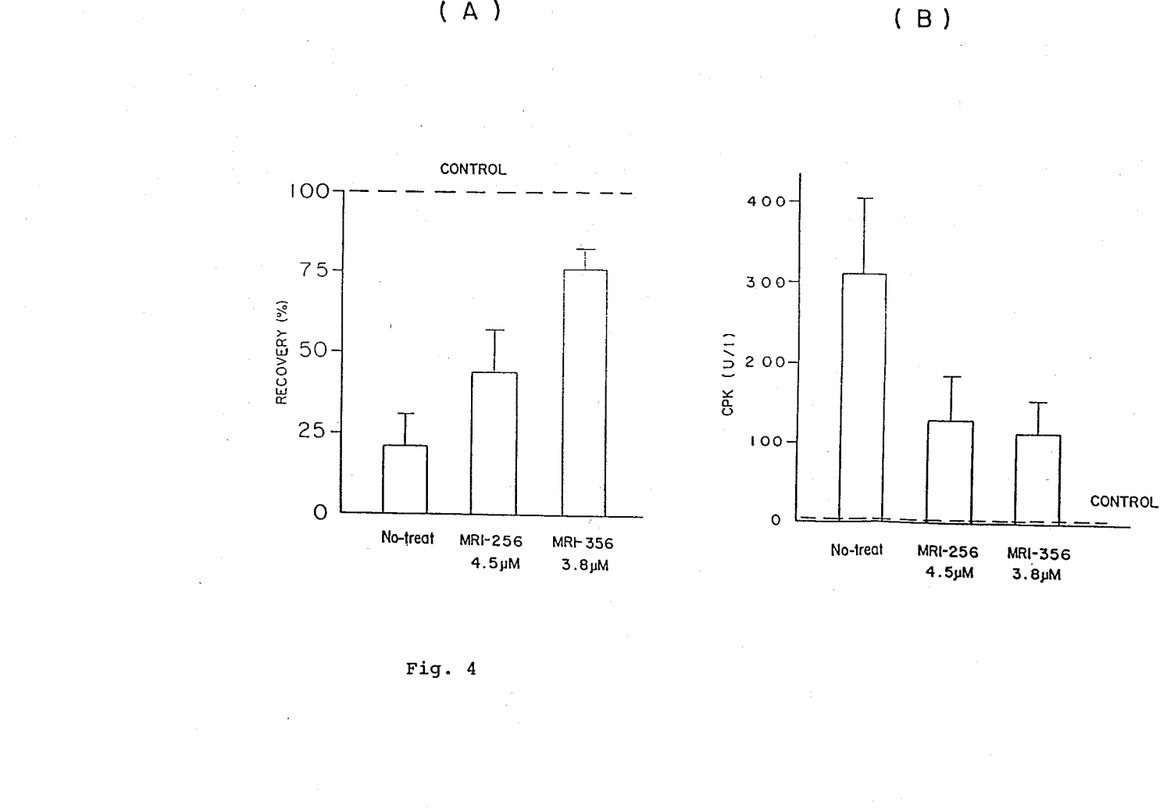

(b) Protection of isolated perfused rat heart:

These drugs protected the isolated beating heart (Langendorff model, FIG. 2) from ischemia. In this experiment, an isolated rat heart was mounted by tieing the aorta to a catheter. Then a modified Krebs-Henseleit solution (117 mM NaCl, 6 mM KCl, 2.5 mM CaCl$_2$, 1.2 mM MgCl$_2$, 2.4 mM phosphate, 24 mM NaHCO$_3$, 5 mM glucose; bubbled with 95% O$_2$—5% CO$_2$ gas; temperature 37°; ph 7.4) was circulated by a pump (flow rate: 15 ml/min). The heart was stimulated 3 beats/seconds by electric pulse (10 V; 10 m sec duration). This system supported the beating heart for more than several hours. The left ventricular output (P) was measured by inserting a catheter with a small latex balloon attached at the tip, and by connecting the catheter to a Statham pressure transducer P23Gb (FIG. 2). After equilibration, the flow of Krebs-Henseleit solution was stopped for 15 minutes. If no drug was added, the heart could hardly beat after the flow was restarted (the cardiac output recovered only to 10–15% of the original level; FIG. 3A). However, if 3.8 uM MR-356 was added before restarting the flow, the heart recovered more than 75% (FIG. 3B). Thus, the drug was able to protect the heart from the "reflow" damage. Protective effects of MR-356 and MR-256 are shown in FIG. 4(A).

(c) Suppression of CPK level:

Another method of measuring protective effect of drugs is to assay the creatine phosphokinase activity (CPK activity) of the circulating solution. When the heart was damaged by ischemia, the CPK activity appeared into the circulating solution after the reflow (see no-treat experiment in FIG. 4(B)). However if drugs were added before the reflow, the level of CPK activity was much reduced

EXAMPLE 2

EFFECT OF DRUGS ON LIVER ISCHEMIA

Figure 5:
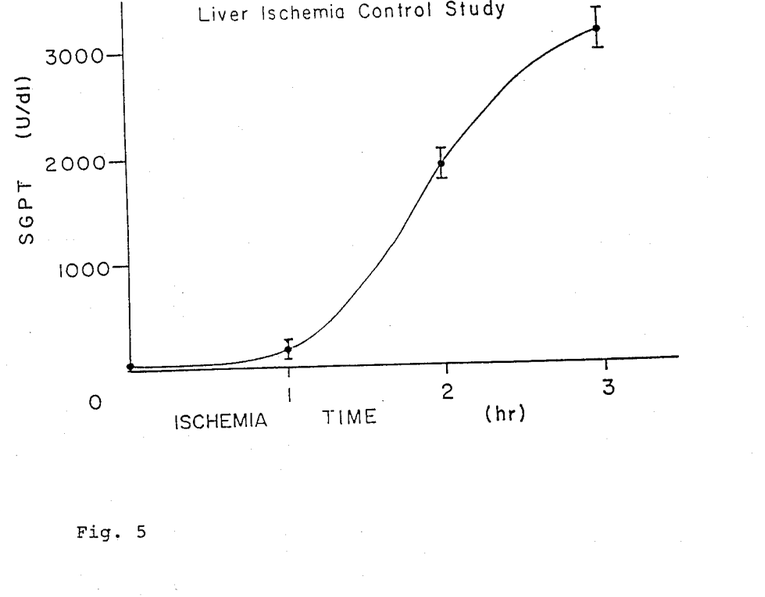
FIG. 5 Effect of global liver ischemia on the level of SGPT. Abscissa indicates the ischemia time. Blood samples were taken 24 hours after ischemia for SGPT assay.
Figure 6:
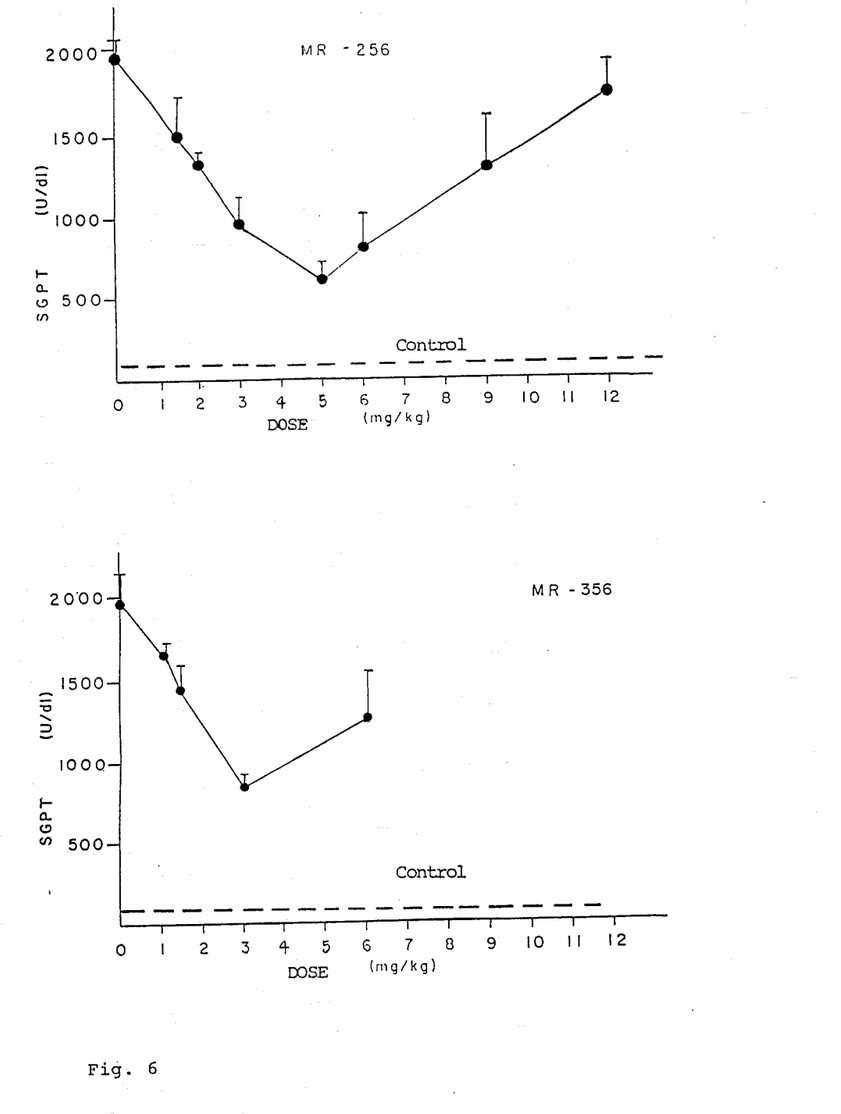
FIG. 6 Dose-response relationship of the effects of MR-256 (upper panel) and MR-356 (lower panel) against the increase of SGPT level caused by 2 hour global liver ischemia (samples were taken 24 hours after the ischemia). The non-ischemia control levels were shown by dashed lines.

Rats weighing 150 to 175 grams were used. Under enflurane anesthesia, a microvascular clamp was placed to occlude the portal vein as well as the hepatic artery, which supplies blood to the left lateral and median lobes of the liver. The rats were subjected to ischemic conditions ranging from 1 to 3 hours, after which reperfusion of the liver is allowed by removing the clamp. Twenty four hours later, blood samples were drawn for the SGPT (serum glutamate-pyruvate transaminase) assay. As shown in FIG. 5, after 2 or 3 hours ischemia the SGPT level steeply increased (to levels of 2,000 to 3,000 U/dl) from the control level which is about 100 U/dl. Using 2 hours of ischemia, we tested the effects of the drugs as shown in FIG. 6. Both MR-256 and MR-356 suppressed the increase of SGPT levels by 60 to 70%. The maximum effect was observed around 3 to 5 mg/kg body weight.

EXAMPLE 3

PROTECTION OF KIDNEY ISCHEMIA

Figure 7:
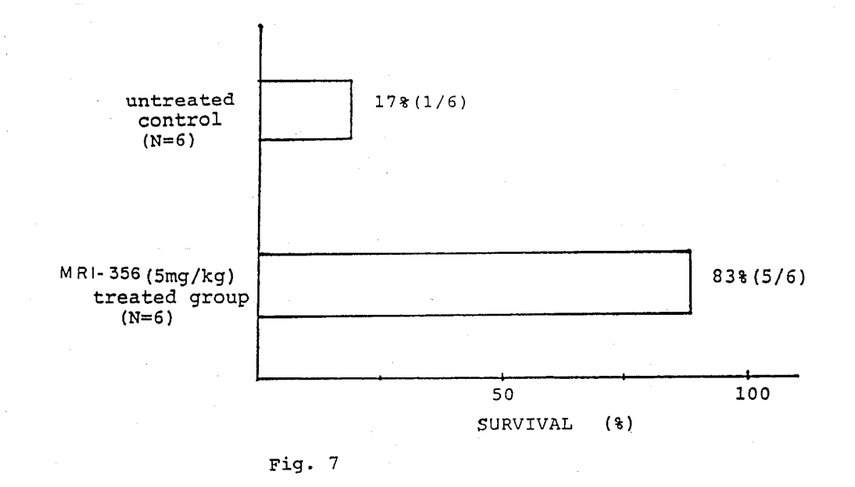
FIG. 7 Effect of MR-356 (5 mg/kg) on the survival rate of rats exposed to global kidney ischemia for 70 minutes. The survival rate was improved when MR-356 was administered.

Experiments were performed on male Sprague-Dawley rats. Both kidneys were exposed through a mid-line incision and the left renal artery was occluded with a microvascular clip to induce a 70 minutes ischemia. After this period, the right kidney was removed, and left renal blood flow was re-established; the incision was closed and the rat was allowed to recover. In the drug-treated groups, intravenous infusion of MR-356 (5 mg/kg) was started 30 minutes prior to renal artery occlusion and continued throughout the ishcemia time and 30 minutes after the ischemia. The protective effect of the drug on the acute renal failure was shown in FIG. 7. By 70 minute global ischemia, only 17% of untreated rats survived for 4 days. However, if the rats were given the drug, 83% were able to survive for 4 days.

EXAMPLE 4

EFFECTS OF DRUGS ON BRAIN ISCHEMIA (a) Surgical procedures:

Adults male Sprague-Dawley rats weighing 250–300 g were used to prepare focal ischemia model developed by Chen et al. (Stroke 17:738–743, 1986). Anesthesia was induced and maintained with halothane (1.0–2.5%) via a closely fitted facial mask. Bilateral common carotid arteries (CCA) were exposed gently and the right CCA was ligated in two places by 4–0 silk suture. To expose the right middle cerebral artery (MCA), the temporal muscles were cut and retracted, then, a small temporal craniotomy (2×2 mm) was performed with a microdrill. Under a microscope, the dura matter was opened with a 26 guage needle, and the MCA was ligated by 10-0 suture with a square knot. Immediately, the left CCA was occluded by a microaneurysmal clip. After the operation, the animal was returned to its cage. One hour later, the left CCA clip was released in awake condition. The sham-operated control was produced in a similar procedure, except for the ligations and clipping of vessels. The operation was usually finished within 30 min.

(b) Water content and ionic analysis:

After fixed time intervals (1, 3, and 7 days), the animal was sacrificed and the excised cerebral hemisphere was placed in a preweighed crucible and measured an wet weight (W.W) with a chemical balance (Mettler, AE 100). The sample was then dried in a oven at 105° C. until it reaches a constant weight, which is defined as a dry weight (D.W). The water content (% wet weight) was calculated by (W.W—D.W.)/W.W.

Figure 8:
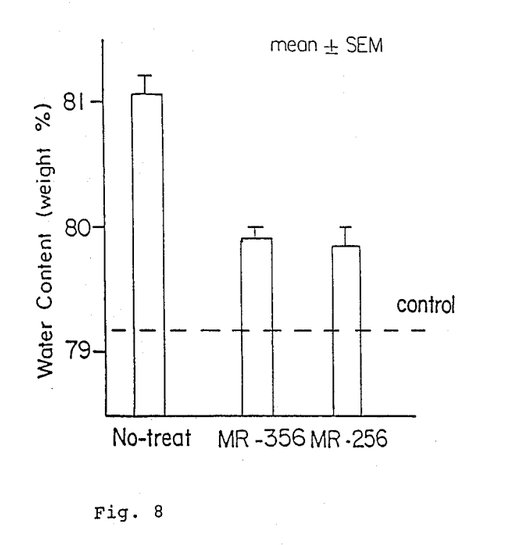
FIG. 8 Increase of the water content of rat brain hemisphere by 1 hour focal ischemia. The water content increased from the control level (which is shown by the dashed line). MR-356 and MR-256 inhibited the increase of water content.

The water content of the right hemisphere (ischemia side) was increased, showing that the brain edema was developed. If drugs (3 mg/kg) were administered i.v. thirty minutes prior to the ischemia insult, the increase of water content was much reduced as shown in FIG. 8.

(c) Motor performance test:

The disturbance of motor functions was evaluated by the total score obtained from the inclined plate test, balance beam test, and prehensile test. These motor performance tests were designed to quantify the motor weakness in the global ischemia rats. We partially modified the original method to suit to the rat focal ischemia model employed in this study, whose motor deficits may be less severe than that of global ischemia (4-vessel occlusion, 20 min). Two trials were given to the animal, and the better score was chosen as its data. To lessen the factor of fatigue, the trial was carried out with a few minutes interval. In the inclined plate test, a 60×30 cm board covered with a thin rubber pad was used as a plate and was fixed at a designated angle (55°). The animal was placed at the highest position of the plate and the time which it could stay on the plate was measured until 30 sec. In the balance beam test, a wooden rod, 70 cm long and 3.2 cm diameter was positioned horizontally 60 cm above a thick sponge pad and the animal was left at the center of rod. The time that the rat spent on the rod was recorded until 30 sec. In the prehensile test, a nylon rope, 70 cm long and 4 mm in diameter, was stretched horizontally 60 cm above a thick sponge pad and the rat's forepaws were placed on the rope and then released. The time that the rat spend hanging on the rope was measured until 30 sec. The scoring methods in these three tests were identical and defined as follows; 0:0 sec; 1:1–10 sec; 2:11–20 sec; 3:21–30 sec; 4: above 30 sec. Therefore, the total motor score ranged from 0 to 12 points.

Figure 9:
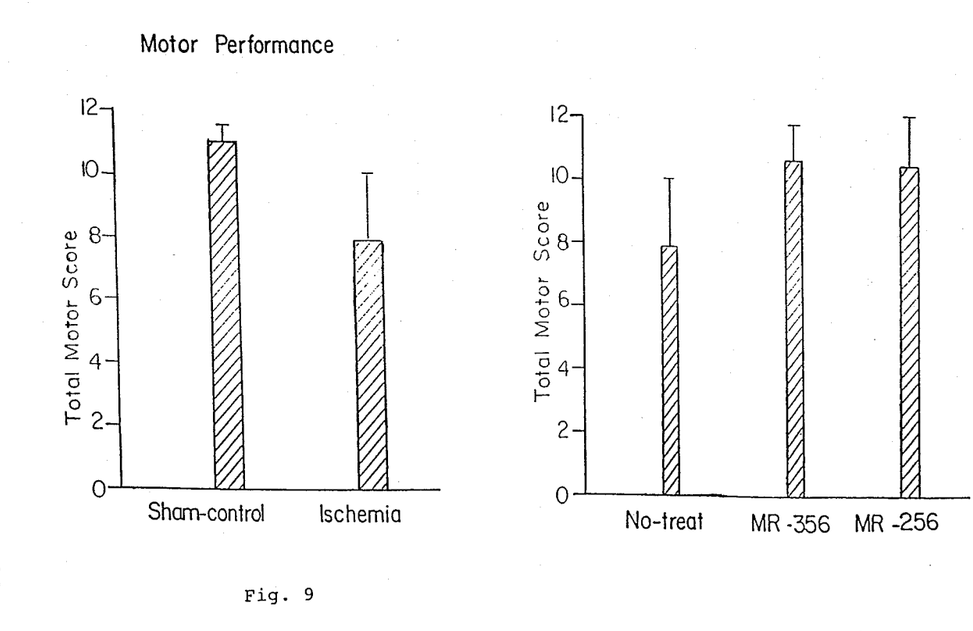
FIG. 9 Effects of ischemia and drugs on motor performance of rats exposed to 1 hour brain focal ischemia. Measurements performed 7 days after ischemia. Note that ischemia decreased the total motor score, but MR-356 and MR-256 reversed the decrease.

FIG. 9 shows the motor function as determined by three tests (complete paralysis is indicated by motor score 0, and normal condition as 12). By focal ischemia, 3 days later, the animal lost about 50% of motor ability as indicated by the motor score of 7 in non-treated animals. In 7 days, animals recovered to approximately the score of 8. With these drugs given before ischemia (3 mg/kg), the motor score obtained 7 days after the operation was about 11 indicating that animals were almost completely recovered (they may still have slight motor deficits).

(d) Passive avoidance test:

The apparatus consists of an illuminated large compartment (40×40 cm) and a dark small compartment (10×10 cm). Grids made of metal conductors were placed at the bottom of the small compartment. Two compartments were connected through an opening (6×6 cm). The rat was placed on a fixed location in the large compartment and was allowed to explore the apparatus for 180 seconds. The time spent in the small compartment was recorded with a stop watch. Then, when the rat was in the small compartment, the opening was closed with a transparent shutter and the rat received a weak electric shock for 30 sec (to a degree that the rat felt a slight pain). By this method, the rat had an experience of fear (learning) and passive avoidance reaction was established. The retention test was undertaken in the same manner as the first exploration 24 hours after the initial test.

Figure 10:
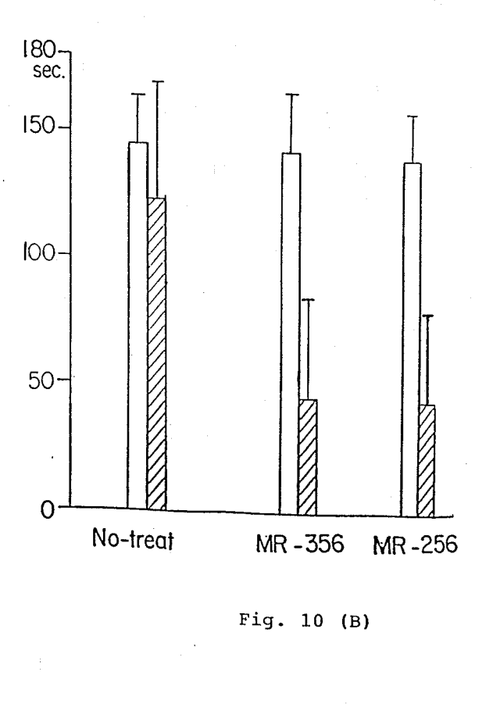
FIG. 10 Experiment of memory disturbance by passive avoidance test. (A) Control rats maintained memory so that they did not go back to the dark room after they learned about electric shock. However in ischemia rats, the retention time (the total spending time in the dark room after having learned the shock) was more than 120 seconds indicating that memory was disturbed. (B) By injecting MR-356 or MR-256 (3 mg/kg) 30 minutes before ischemia, the retention time was remarkably decreased indicating that their memory was retained.

After receiving the electric shock, normal rats remembered the pain and never went back to the dark room again (retension time was 0). However, in ischemia rats, their memory was disturbed; they went back into the dark room. FIG. 10(A) shows that ischemic rats spent approximately 120 seconds in the dark room (as shown by shadowed column of retention time).

When the drugs were administered before the ischemia, animals maintained better memory as shown in FIG. 10(B). The retention time was significantly decreased (to 40 to 50 seconds).

EXAMPLE 5

SPINAL CORD INJURY

In spinal cord injury, the primary injury is accompanied by immediate loss of nerve action potential and rapid ion movement. This is followed by secondary events which result in cell death in a matter of hours. It was found that drugs developed by the inventor were able to interrupt the chain of events that lead to cell death.

(a) Experimental procedure:

A method developed by Wrathall's group (Wrathal et al. Exper. Neurology 88:108–122, 1985; Noble, L. J. and Wrathall, J. R. Exper. Neurology 95:530–533, 1987) was used. Animals were anesthetized with nembutal (50 mg/kg). Laminectomy was performed on the T-11 segment of the spinal cord. The skin wound was temporarily closed and the animal was recovered from the effect of laminectomy. Several hours later, the animal was anesthesized with 1.5% halothane (air as a carrier). The T-11 segment was again exposed and an impounder (made of plastic with a tip diameter of 2.4 mm) was placed on the exposed dura. Then, a 10 gram weight was dropped from the height of 5 mm onto the impounder. The impounder remained on the surface of the spinal cord for a few seconds, after which it was removed. The skin wound was sutured closed. The animal was returned to the cage after regaining consciousness. The bladders were compressed twice daily to induce urination.

Figure 11:
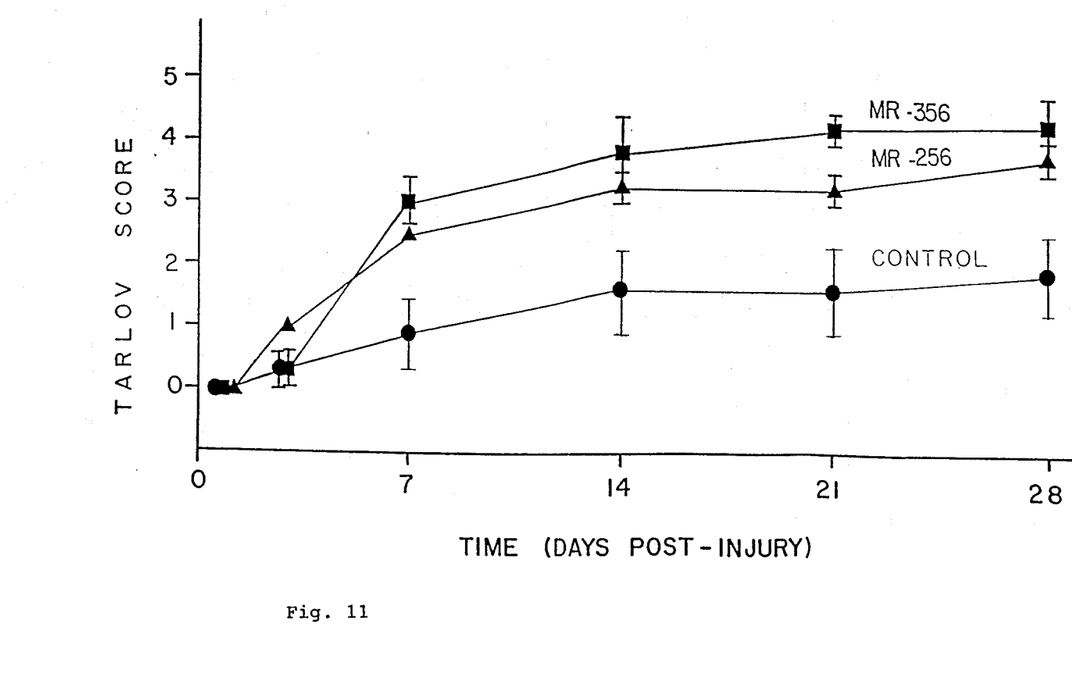
FIG. 11 Motor performance as measured by Tarlov Score with rats which received dynamic contusion injury on the spinal cord. In control (no drug) experiment, rats were still paralyzed after 4 weeks, while post-injury administration (5 mg/kg i.v. each at 0.5, 6, and 12 hours after injury) of MR-356 or MR-256 remarkably improved their performance. MR-356 was more effective than MR-256.

(b) Assessment of motor recovery: After contusion, animals were observed for four weeks during which time the recovery was quantified by rating the hindlimb walking ability according to the method originally used by Tarlov (Tarlov, I. M. Arch. Neurol. psychiatry 71:588–597, 1954) and modified by Wrathall et al. (Exper. Neurology 88:108–127, 1985). This is basically a scoring system for hind limb mobility ranging from 0 to 5. Zero indicates complete paralysis, while a score of 5 indicates full recovery. As shown in FIG. 11, measurements were taken from a group of rats receiving no treatment (control) and a group receiving drug treatment after injury. The drug was administered i.p. three times; 0.5, 6 and 12 hours after injury (each time 5 mg/kg body weight). As shown in FIG. 11, both MR-256 and 356 improved the recovery, but MR-356 was more effective.

EXAMPLE 6

SICKLE CELL ANEMIA

The inventor previously developed the method to produce irreversibly sickled cells (ISC, which are irreversibly denatured sickle cells) by exposing sickle red blood cells to a repeated sickling-unsickling cycling in vitro. He used this system to determine the efficacy of drugs in protecting cell membranes (Ohnishi, Br. J. Haematol. 55:665–671, 1983; Ohnishi et al. Biochim. Biophys. Acta 886:119–129, 1986). When sickle cells were exposed to a sickling-unsickling cycling for 3 hours, about half of the cells were denatured as revealed by the formation of heavy, dehydrated cells in density gradient centrifugation. These heavy cells were collected, the amount measured, and the percentage of production calculated (Table 1). As shown in the Table, when 13 uM of MR-356 was added, the formation of irreversibly denatured cells was remarkably inhibited. MR-256 was less effective; even with 40 uM, formation of irreversibly denatured cells was not much inhibited (Table 2).

TABLE 1

Protective effect of MR-356 against the formation of irreversibly sickled cells caused by sickling-unsickling cycling (numbers indicate the percentages)

| | drug during cycling | | | no cycling |
|---|---|---|---|---|
| | 0 | 13 | 40 uM | 0 uM |
| Reversibly sickling cells | 52.3 | 93.1 | 100 | 100 |
| Irreversibly sickled cells | 47.7 | 6.9 | 0 | 0 |

TABLE 1-continued

Protective effect of MR-356 against the formation of irreversibly sickled cells caused by sickling-unsickling cycling (numbers indicate the percentages)

| | drug during cycling | | | no cycling |
|---|---|---|---|---|
| | 0 | 13 | 40 uM | 0 uM |
| sickled cells | | | | |

TABLE 2

Protective effect of MR-256 against the formation of irreversibly sickled cells caused by sickling-unsickling cycling (numbers indicate the percentages)

| | drug during cycling | | | no cycling |
|---|---|---|---|---|
| | 0 | 13 | 40 uM | 0 uM |
| Reversibly sickling cells | 55.7 | 64.6 | 74.8 | 100 |
| Irreversibly sickled cells | 44.3 | 35.4 | 25.2 | 0 |

EXAMPLE 7

MALARIA

Figure 12:
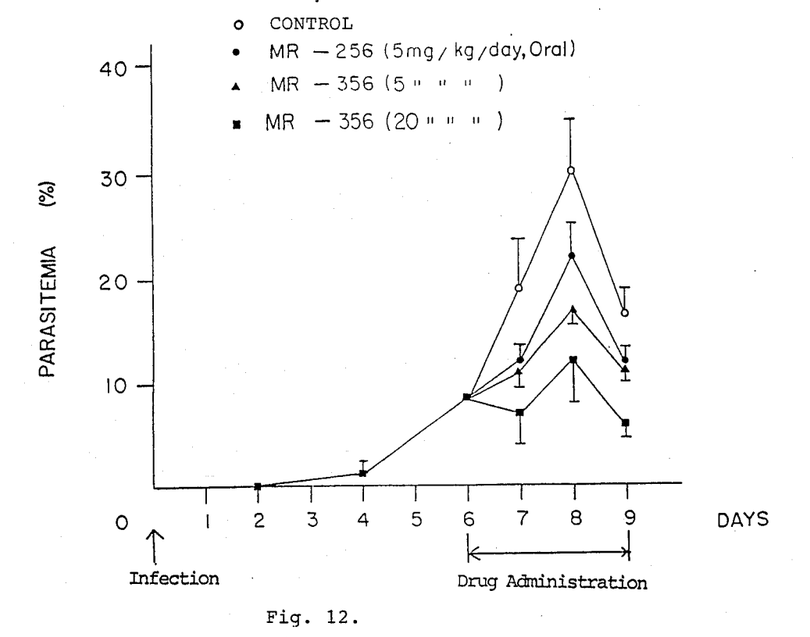
FIG. 12 Inhibitory effect of drugs (oral administration for 3 days) on malarial parasites. Mice were infected by $P.$ $Chaubaudi$ on day 0 by $10^6$ parasitized red cells. MR-356 was more effective than MR-256 in inhibiting the growth of malarial parasites.
Figure 13:
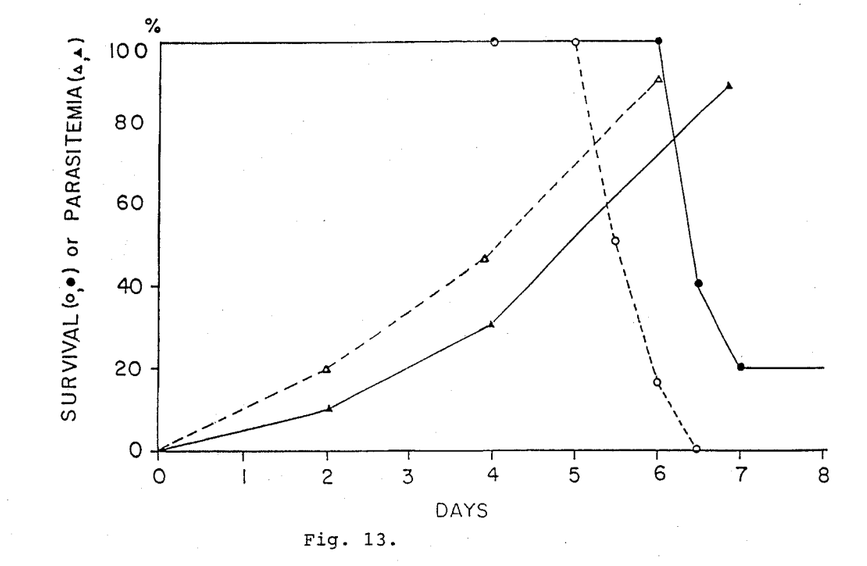
FIG. 13 Inhibitory effect of MR-356 (2 mg/kg/day i.p. once a day) on the survival rate (circular symbols) and parasitemia (triangular symbols) of mice infected by $P.$ $Vinckei$ ($10^6$ parasitized red cells on day 0). Open symbols stand for no-drug treatment and filled symbols stand for drug-treated animals. MR-256 was not effective on $P.$ $Vinckei$ (data not shown).

Two different kinds of plasmodium were tested: *Plasmodium Chabaudi* and *Plasmodium Vinckel*. In the *P. Chabaudi* experiment, the increase of parasitemia was measured after each mouse was infected by $10^6$ parasite-infected red blood cells. After 8 days, the parasitemia in the non-treated group was almost 30%. As shown in FIG. 12, the effect of MR-256 was not significant, but the increase of parasitemia was almost completely inhibited by MR-356 (20 mg/kg per day). In case of *P. Vinckel*, the survival rate was also measured together with parasitemia. Since this parasites are so strong, they kill all mice in the end. As shown FIG. 13, infection by $10^6$ parasite-infected red blood cells killed mice in the control group in 6 and a half days. However, with MR-356 (2 mg/kg per day), the survival time was prolonged, and 20% of animals survived. The rate of increase of parasitemia was also inhibited by MR-356 as shown in the figure. In *P. Vinckel* experiments, MR-256 did not show any beneficial effect.

FIGURE LEGENDS

FIG. 4(A). Recovery of left ventricular output after 15 minutes ischemia. Drugs were given before reflow. Ischemia time was 15 minutes. In control (non ischemia) experiments, the output level was maintained for many hours. (B) Increase of CPK level in the perfusates collected 15 minutes after the start of reflow (following 15 minutes of ischemia). When there was no drug, the CPK level increased by ischemia. However, if drug was given before the reflow, the CPK level was much reduced.

I claim:

1. A method for preparing hydrophobic esters selected from the group consisting of acetoxymethyl and acetoxyethyl esters, said method comprising using oligomers, which are prepared from starting materials, selected from the group consisting of prostaglandin $A_1$ and prostaglandin $E_1$ modified by the addition of an alkaline hydroxide material; said method further comprising combining 50 mg of one of the starting materials with 0.5 ml of ethyldiisopropylamine, 0.1 ml chloroform and 2 ml of iso-alcohol; adding 0.2 ml of acetoxymethyl bromide or acetoxyethyl bromide to the mixture and stirring in a stoppered flask for 20 hours evaporating said stirred materials in vacuo, taking up the residue in benzene, and filtering to remove unnecessary byproduct (ethyldiisopropylammonium bromide); reevaporating the benzene solution; extracting the residue with diethyl ether; and evaporating the extract in vacuo overnight.

2. A method of protecting vital organs, such as the brain, spinal cord, heart, lung, liver, kidney, stomach, duodenum and blood vessels against damage caused by (a) ischemic, and (b) spinal cord injuries by administering the ester-compounds of claim 1
   (a) orally at a dosage of 10 mg/kg body weight/day or
   (b) subcutaneously or intramuscularly at a dosage of 6 mg/kg body weight/day or
   (c) intravenously at a dosage of 2 mg/kg body weight/day.

3. The method of claim 2 involving protecting organs from deterioration during transplant surgery by administering the ester-compounds of claim 1, to the donor prior to the organ removal at dosages given claim 2, and by administering these compounds to the receipient after the organ transplant at dosages given in claim 2.

4. The method of protecting blood cells by administering compounds of claim 1 at dosages given in claim 2.

5. The method of claim 4 involving protecting red blood cells of sickle cell anemia patients by administering compounds of claim 1 at dosages in claim 2.

6. The method of claim 4 involving protecting red blood cells from attack of malarial parasites by administering compounds of claim 1 at dosages in claim 2.

* * * * *